(12) United States Patent
Schmieding et al.

(10) Patent No.: US 6,663,656 B2
(45) Date of Patent: Dec. 16, 2003

(54) TORQUE DRIVER FOR INTERFERENCE SCREW

(75) Inventors: Reinhold Schmieding, Naples, FL (US); Philip S. O'Quinn, Naples, FL (US); Peter Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 177 days.

(21) Appl. No.: 09/948,670

(22) Filed: Sep. 10, 2001

(65) Prior Publication Data

US 2002/0120275 A1 Aug. 29, 2002

Related U.S. Application Data (60) Provisional application No. 60/270,865, filed on Feb. 26, 2001.

(51) Int. Cl.[7] ............................................... A61F 02/08
(52) U.S. Cl. .................................... 606/232; 623/13.11
(58) Field of Search ................................ 606/104, 232, 606/72, 73; 623/13.11, 13.14

(56) References Cited

U.S. PATENT DOCUMENTS

| | | | | |
|---|---|---|---|---|
| 5,871,504 A | * | 2/1999 | Eaton et al. | 606/232 |
| 5,891,146 A | * | 4/1999 | Simon et al. | 606/71 |
| 5,957,953 A | * | 9/1999 | DiPoto et al. | 606/232 |
| 6,478,795 B1 | * | 11/2002 | Gournay et al. | 606/61 |
| 6,517,579 B1 | * | 2/2003 | Paulos et al. | 623/13.14 |
| 2001/0007074 A1 | * | 7/2001 | Strobel et al. | 606/73 |

\* cited by examiner

*Primary Examiner*—Kevin Shaver
*Assistant Examiner*—Michael B. Priddy
(74) *Attorney, Agent, or Firm*—Dickstein, Shapiro, Morin & Oshinsky, LLP (57) ABSTRACT

A torque driver includes a torque measurement assembly for indicating the amount of torque being applied during implanting of an interference screw. The torque measurement assembly includes a proximal cup and a distal cup, and a coil spring fixed between the cups. A torque scale is marked on one of the cups, while a reference marking is provided on the other. When used to insert an interference screw, the driver head is inserted into the socket of the screw and the driver is turned, which causes the torque spring to tighten. As the spring tightens, the reference mark moves relative to the scale to indicate the torque measurement exerted on the spring. Using this torque driver, a surgeon can be made aware if too much torque is being exerted or if a desired minimum torque load for achieving a desirable level of fixation strength for the graft is not reached.

6 Claims, 7 Drawing Sheets

TORQUE DRIVER FOR INTERFERENCE SCREW

This application claims the benefit of U.S. Provisional Application No. 60/270,865, filed Feb. 26, 2001, the disclosure of which is herein incorporated by reference.

BACKGROUND OF THE INVENTION

1. Field of the Invention

The present invention relates to instrumentation used for endosteal fixation of a substitute ligament and, more specifically, to a driver for inserting a tapered bioabsorbable interference screw to perform soft tissue attachment to bone such as arthroscopic endosteal fixation of a substitute anterior cruciate ligament.

2. Description of the Related Art

When a ligament becomes detached from a bone, surgery usually is required to reconstruct the ligament. Often, a substitute ligament or graft is secured into bone tunnels to facilitate incorporation and permanent attachment. It is critical that the reattached tissue or the tissue graft be sufficiently secured to withstand the normal loads to which they may be subjected, e.g., those imposed by a patient on the affected joint or region.

Various methods of graft attachment are known, including the use of interference screws to secure the graft against the walls of a tunnel drilled through the tibia and a socket formed in the femur. A strong graft attachment is obtained by using a metal interference screw to wedge a graft bone block to the wall of a graft tunnel formed through the bone, as disclosed in U.S. Pat. No. 5,211,647 to Schmieding. If a bioabsorbable interference screw is used, the graft is often wedged directly against the bone by the screw, without a bone block.

Bioabsorbable interference screws are usually sized so that they are slightly larger than the diameter of the tunnel, so that they dilate the bone tunnel upon insertion. Dilation advantageously compacts the soft cancellous bone between the ends of the tunnel, providing better fixation. Conventional straight-sided bioabsorbable interference screws have an interference fit of about 1 mm. meaning that about 1 mm of bone is dilated as the screw is inserted into the bone tunnel.

Recent tests have determined that a relationship exists between screw insertion torque and graft fixation strength when inserting interference screws. As disclosed in the study entitled "Correlation of Insertion Torque, Load at Failure and Bone Density Utilizing a Soft Tissue Interference Screw with Free Central Quadriceps Tendon Graft in ACL Reconstruction," presented at the 1999 International Society of Arthroscopy, Knee Surgery and Orthopedic Sports Medicine Congress by J. P. Fulkerson et al., the correlation of insertion torque to peak load at failure was calculated to be 0.86, and that the fixation strength achieved in each instance in which the insertion torque was greater than 14.5 in/lbs. resulted in a peak load greater than 315 N at failure.

Greater insertion torque can be achieved by increasing the resistance of the interference screw being inserted into the tunnel. Thus, a larger diameter screw relative to the diameter of the bone tunnel provides greater dilation and a greater interference fit, and therefore increased fixation strength. Some larger, conventionally-shaped interference screws, however, have larger tips and are more difficult to align and insert correctly. One example of a bioabsorbable interference screw which provides increased dilation and interference fit without increased difficulty of insertion is disclosed in pending U.S. patent application Ser. No. 09/711,964 filed Nov. 15, 2000 and entitled "Tapered Bioabsorbable Interference Screw for Endosteal Fixation of Ligaments," the disclosure of which is herein incorporated by reference.

In light of the recently discovered correlation between insertion force and fixation strength, it would be beneficial if surgeons could determine the amount of force being exerted during insertion of the interference screw or otherwise directly assess the amount of fixation strength provided by the inserted interference screw. If a graft is secured with insufficient fixation strength to withstand expected loads, the patient may experience a limited recovery of the affected joint at best, and may suffer re-injury or separation of the graft from the bone. On the other hand, if too much force is applied to the interference screw during fixation, the bone may become overstressed, resulting in cracks or other damage. Currently, however, no method is available to quantify the torque force exerted during insertion of the interference screw, or to otherwise determine whether or not an acceptable range of fixation strength has been achieved.

SUMMARY OF THE INVENTION

The present invention fills the void in the prior art by providing a torque driver which can measure the amount of torque being applied during implanting the screw. The torque driver according to the present invention is similar to a standard driver known in the art having a handle, drive shaft and drive head, a sleeve disposed around the proximal portion of the shaft, and further includes a torque measurement assembly connected between the handle and the sleeve.

The torque measurement assembly includes a proximal cup and a distal cup, and a coil spring encased between the cups, with one end of the spring fixed in the proximal cup and the other end of the spring fixed in the distal cup. The proximal cup is fixed to the distal end of the sleeve, and the proximal portion of the sleeve is fixed in the handle. The distal cup is fixed to the drive shaft, which rotates freely within the sleeve. Thus, the drive shaft and distal cup move together as one unit while the handle, sleeve, and proximal cup move together as one unit. The two units are physically connected to each other only by the torque spring.

When the torque driver is used to insert an interference screw, the driver head is inserted into the socket of the screw and the driver is turned, the rotational force exerted to drive the screw causes the torque spring to tighten. A torque scale is marked on one of the proximal and distal cups in accordance with the resistance of the torque spring, while a reference marking is provided on the other. As the spring tightens, the reference mark moves along the scale to indicate the torque measurement exerted on the spring.

Since the torque exerted to drive an interference screw into bone is related to the resistance met by the screw in entering the bone, using the present invention, a surgeon can be confident that a desired minimum torque load is being applied which translates to a correspondingly desirable level of fixation strength for the graft. The surgeon is made aware if inadequate fixation strength is measured during fixation of the screw, whereupon backup fixation devices are indicated and can be implanted to secure the graft, or alternatively, an interference screw having a larger diameter can be used instead. Also, the surgeon is made aware if too much torque is being exerted, which creates a risk of splitting or otherwise damaging the bone at the fixation site.

Preferably, though not necessarily, the interference screw used with the present invention is a tapered, elongated bioabsorbable interference screw, the taper of the screw extending along substantially the entire length of the elongated threaded screw. The taper of the bioabsorbable interference screw of the present invention advantageously facilitates insertion of the tip of the screw, while providing superior fixation resulting from an enlarged back end. Upon insertion, the bioabsorbable interference screw of the present invention fills all but 5–10 mm. of the tunnel, thereby providing increased fixation strength while also promoting healing.

Additionally, the preferred interference screw used in conjunction with the present invention includes a head provided with a specially designed Delta drive socket for receiving a Delta drive screwdriver or a traditional hex-head screwdriver. The unique driver socket of the interference screw of the present invention optimizes the torque capacity of the screw. To maintain wall thickness, the drive socket may be tapered in correspondence with the tapered outer profile of the device. The taper also permits easy insertion of the tip and shaft of the Delta driver or hex driver (also tapered if screw drive socket is tapered) into the fixation screw.

The tapered bioabsorbable interference screw usable with the present invention is threaded along substantially the entire length of the screw to maximize fixation strength within the tunnel and is preferably, formed of highly crystalline poly-(L-lactic acid) (PLLA) compound. Also, the distal end of the screw, i.e., the end closest to the joint, has a smooth, rounded tip profile so as to minimize abrasion with the graft.

Optionally, the torque driver and interference screw in accordance with the present invention may be both cannulated for insertion over a guide pin. According to this aspect of the invention, the guide pin is inserted through the cannula of the driver and the interference screw, and into the bone tunnel, to thereby guide the interference screw during delivery and installation.

In an exemplary method of ACL reconstruction of the present invention, the graft, such as a hamstring tendon autograft or allograft, is secured by interference screw fixation in a femoral socket formed through the tibial tunnel, as described, for example, in U.S. Pat. No. 5,320,626, the disclosure of which is incorporated herein. The hamstring graft is then drawn taut and secured in the tibial tunnel by insertion of the interference screw using the torque driver of the present invention.

Other features and advantages of the present invention will become apparent from the following description of the invention which refers to the accompanying drawings.

BRIEF DESCRIPTION OF THE DRAWINGS

FIGS. 16–19 show a quick-connect torque assembly which may be incorporated in the variant of the torque driver of the present invention.

FIG. 20 shows a ratchet handle which may be used in combination with the quick-connect torque assembly feature in a further variant of the present invention.

DETAILED DESCRIPTION OF THE PREFERRED EMBODIMENT

Figure 1:
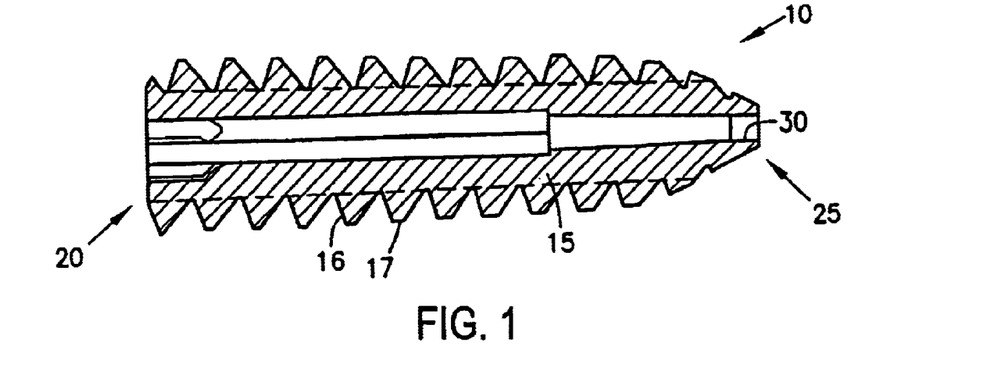
FIG. 1 is a cross-sectional detail view, drawn along line A—A of FIG. 2, of the tapered bioabsorbable interference screw of the present invention.

A cross-sectional view of the preferred interference screw usable with the present invention is the tapered bioabsorbable interference screw 10 as shown in FIG. 1. Screw 10 is formed of a bioabsorbable material, such as PLA or PLDLA (Poly(L/D-lactide)Acid), and may be provided in a variety of lengths, with 35 mm being preferred. Screw 10 has a main body portion 15, a proximal end 20, and a distal end 25, with threads 16 extending substantially from proximal end 20 to distal end 25. The edges 17 of the thread(s) 16 are flattened to prevent severing tissue during screw insertion. Preferably, screw 10 is also provided with a cannula 30 extending centrally therethrough.

Figure 2:
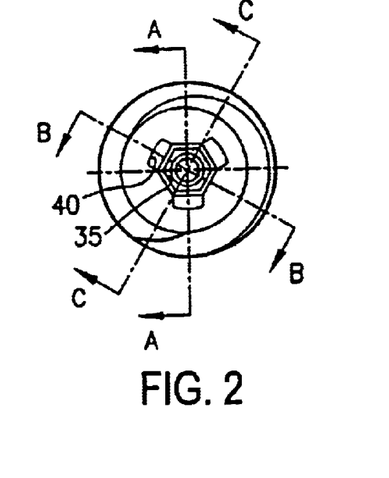
FIG. 2 is a rear elevational view of the tapered bioabsorbable interference screw of the present invention.

Referring now to FIG. 2, the proximal end 20 of screw 10 is provided with an elongated socket 35 configured to receive the torque driver of the present invention, as will be described below. Socket 35 is preferably hexagonal in cross-section along the length thereof, and is furthermore formed, at least at the proximal portion thereof, with radially-extending slots 40 at every other annular face of socket 35. The slots 40 receive correspondingly-shaped protrusions 42 (as best seen in FIG. 5B) on the proximal end of the drive head of the driver. The delta-shaped drive socket 35 permits increased torque capacity while minimizing the problem of stripping the drive portion of the screw 10. Advantageously, the drive socket can also be used with a driver having a traditional hex drive head.

Figure 3:
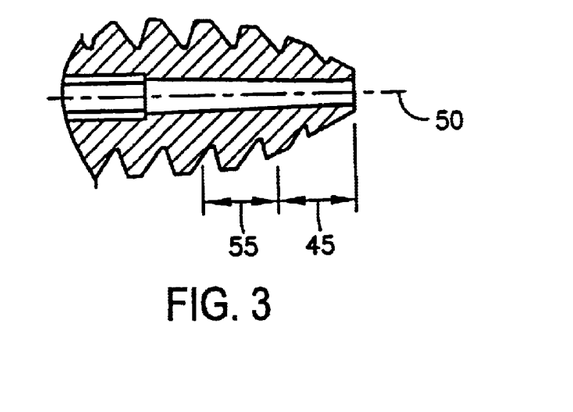
FIG. 3 is a cross-sectional detail view, drawn along line C—C of FIG. 2, of the interference screw of the present invention.
Figure 4:
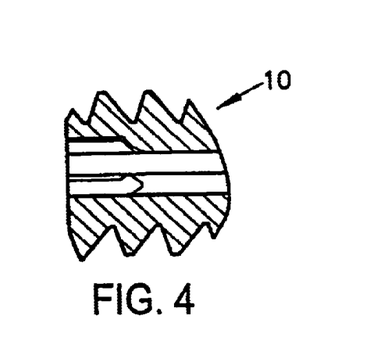
FIG. 4 a cross-sectional detail view, drawn along line D—D of FIG. 2, of the interference screw of the present invention.

As shown in FIGS. 1 and 3, screw 10 is tapered. The taper is a complex taper with an initial portion 45 at an angle of about 27° with respect to the longitudinal axis 50, an intermediate portion 55 at an angle of about 12° angle with respect to axis 50, and an elongated main body 15 with a more gradual taper. The relatively pointed distal portion 45 forms a nose that provides for easy insertion of the screw 10 into a bone tunnel.

The interference screw of the present invention is provided in four sizes: (1) a screw which tapers from a 7.5 mm diameter at its tip to 9 mm. at the socket; (2) a screw which tapers from a 8.5 mm diameter at its tip to 10 mm. at the socket; (3) a screw which tapers from a 9.5 mm diameter at its tip to 11 mm at the socket; and (4) a screw which tapers from a 9.5 mm diameter at its tip to 12 mm at the socket.

As screw 10 threadingly advances through a bone tunnel, the screw dilates bone outwardly around the bone tunnel and creates an interference fit therewith. The tapered body of the screw permits the use of a smaller tunnel, as compared with non-tapered bone screws. The taper also causes a wedge effect that allows a large-diameter screw to be used in relation to the bone tunnel and graft size. Preferably, the interference screw is sized to promote about a 1.5 mm interference fit; i.e., so that the diameter of the proximal end 20 of the screw 15 is 1.5 mm larger than the diameter of the bone tunnel. Typical bone screws, which are not tapered, provide a maximum of 1.0 mm interference fit. The additional interference provides 28% more pull out strength.

Screw 10 is configured to be sufficiently long so as to fill all but the top 5–10 mm of the tibial bone tunnel. This configuration secures a large portion of the ligament graft against the bone tunnel while also providing threading engagement of the threads 16 of screw 10 against cortical bone at outer end of the bone tunnel. Because cortical bone is significantly harder than the interior soft, cancellous core, cortical bone provides significantly more load bearing capability. As a result, proper use of the interference screw described herein eliminates the need for multiple, shorter interference screws in a bone tunnel.

Figure 5A:
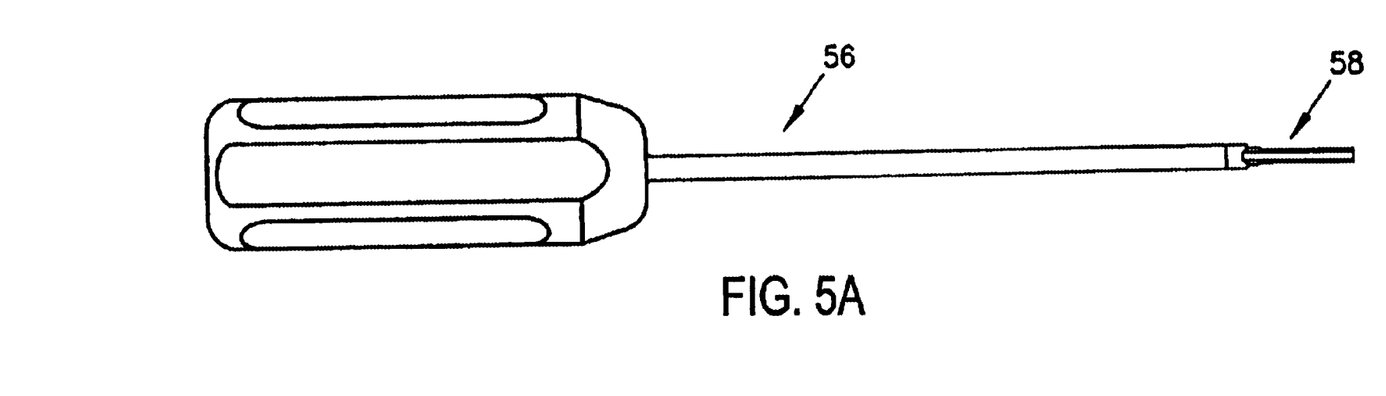
FIG. 5A is a side view of the interference screw driver and FIG. 5B is a detailed view of the tip of the driver.
Figure 5B:
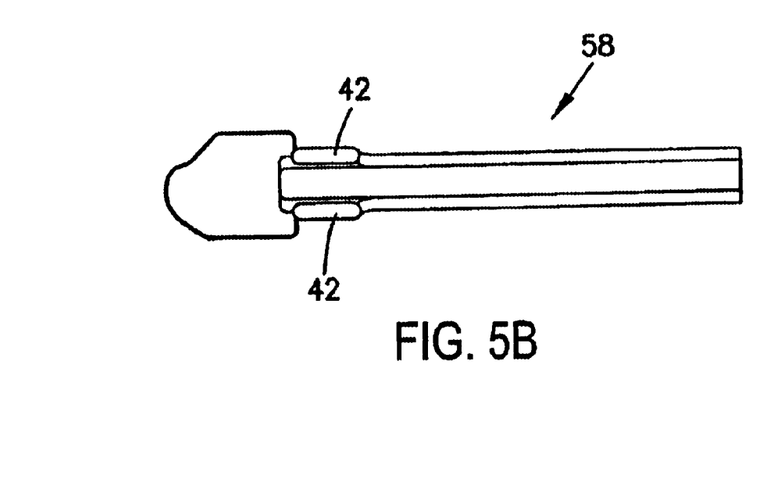

FIGS. 5A and 5B show a prior art driver 56 for inserting interference screw 10. Driver 56 has a handle and a drive shaft with an elongated hexagonally shaped drive head 58 forming the distal portion of the shaft. The hexagonal drive head is best shown in the magnified view illustrated in FIG. 5B, and is provided with protrusion 42 to mate with the delta-shaped drive recess 35 of screw 10.

Figure 6:
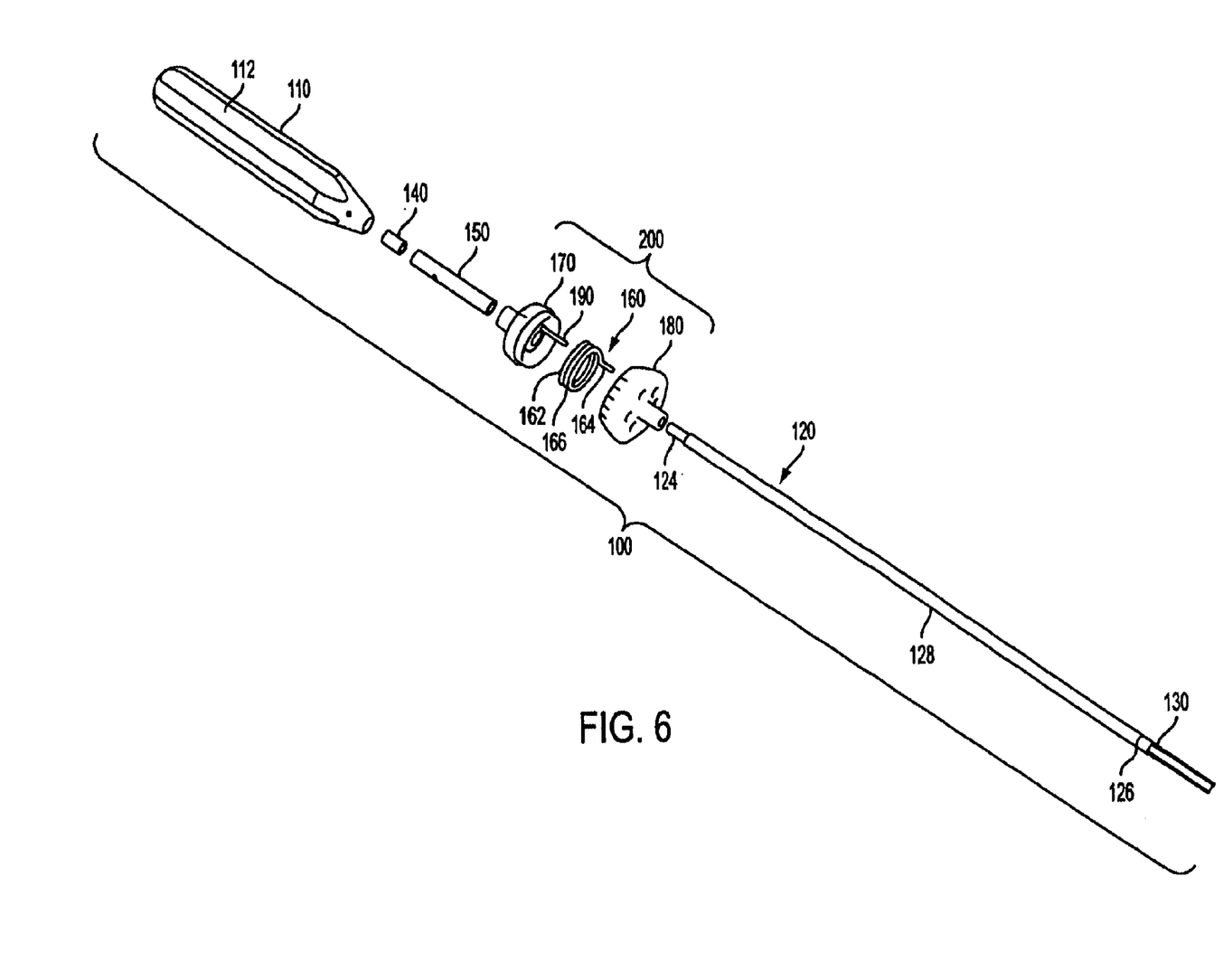
FIG. 6 is an exploded perspective view of a torque driver in accordance with the present invention.
Figure 7:
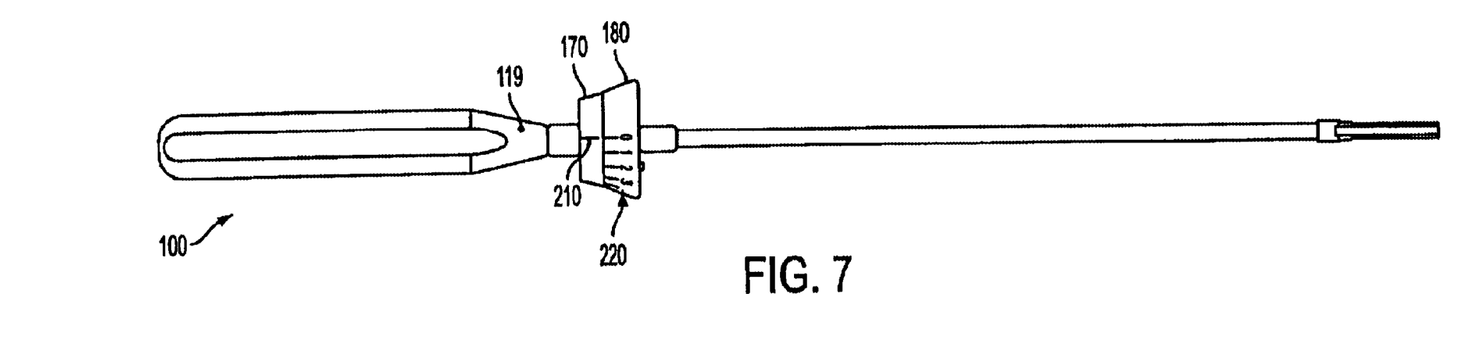
FIG. 7 is a side elevational view of the torque driver of FIG. 6.
Figures 8, 9:
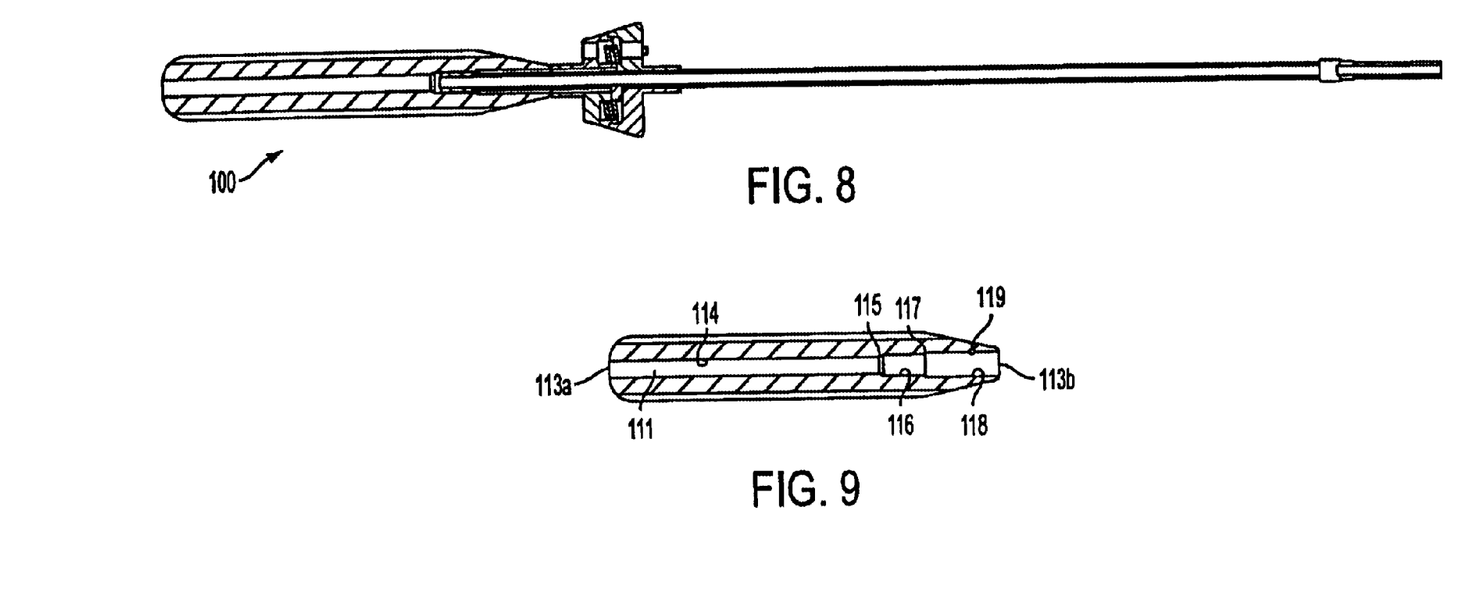
FIG. 8 is an axial cross-sectional view of the torque driver of FIG. 6.
FIG. 9 is an axial cross-sectional view of the handle of the torque driver of FIG. 6.

The torque driver 100 according to the present invention is an improvement over the prior art driver, and is shown in exploded FIG. 6. FIG. 7 is an elevational view of the torque driver, while FIG. 8 is a cross-sectional view of the torque driver. Torque driver 100 generally includes a handle 110, a drive shaft 120 and a drive head 130, as in the prior art driver, and further includes a collar 140, a sleeve 150 and a torque assembly 200.

As shown in FIG. 9, handle 110 has axial grooves 112 (FIG. 6) and a central bore 111 extending through the length of the handle for receiving a guidewire therethrough (so as to be usable with the optionally cannulated interference screw). Central bore 111 has three distinct segments each of constant diameter along its respective length. First segment 114 extends from opening 113*a* at the proximal end of the handle 110 to approximately three-quarters of the length of the bore 111. Adjoining the distal end of segment 114, the diameter of bore 111 increases to that of second segment 116 via a radially outwardly tapered region 115. Adjoining the distal end of segment 116, the diameter of bore 111 increases further to that of third segment 118 via a stepped shoulder 117. Third segment 118 extends to the opening 113*b* at the distal end of handle 110. A small hole 119 is formed at the distal portion of handle 110 from the outer surface of the handle extending into third segment 118 to accommodate insertion of a press fit pin (not shown), the purpose of which will be described later.

The diameter of the second segment 116 is slightly larger than the outer diameter of collar 140 so as to receive collar 140 with sufficient room for rotation therein, but smaller than the outer diameter of sleeve 150. Similarly, the diameter of the third segment 118 is sized to receive sleeve 150 therein.

As can be seen in FIG. 8, shaft 120 has a cannula extending through the length thereof to allow a guide wire to be threaded therethrough, and further includes a proximal portion 124 (FIG. 6) having a reduced diameter relative to the main portion 128 thereof, and a drive head 130 at the distal end thereof. As in the prior art driver, the drive head 130 includes an elongated hexagonally shaped shaft at its distal end and having protrusions to mate with the drive recess of the bio-interference screw. The cannula extending centrally through shaft 120 also extends through the distal tip of drive head 130 to accommodate a guide wire.

The inner diameter of sleeve 150 is sufficiently larger than the outer diameter of the main portion 128 of drive shaft 120 to enable the shaft to rotate freely therein, while the outer diameter of sleeve 150 is sized to be fitted in the third segment 118 of cannula 111.

Collar 140 has an inner diameter sized to be fitted over the reduced diameter portion 124 of shaft 120, and an outer diameter which enables collar 140 to be rotated in second segment 116 of cannula 111 without frictional resistance.

Torque assembly 200 includes a proximal cup 170 and an distal cup 180 encasing a torque spring 160 and a guide pin 190.

Torque spring 160 is a coil spring in which the coil ends are bent to form two legs 162, 164 extending parallel to the coil axis in opposite directions away from the coiled body 166.

Figure 10:
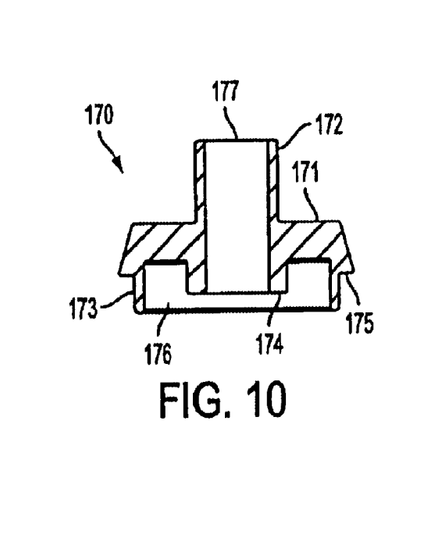
FIG. 10 is a cross-sectional view of the proximal cup of the torque assembly in the torque driver.
Figure 11:
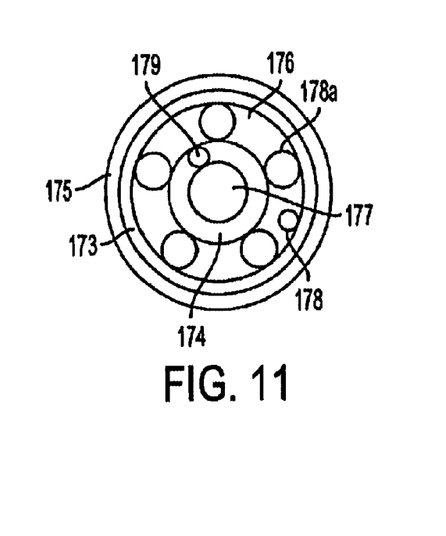
FIG. 11 is a distal elevational view of the proximal cup of the torque assembly.

Referring now to FIGS. 10–11, proximal cup 170 is formed as an integral unit having a main body 171, stem 172 formed on one side of main body 171, outer cylindrical wall 173 formed on the opposite side of main body 171, inner cylindrical wall 174 formed opposite to stem 172 on the same side of main body 171 as outer cylindrical wall 173, and shoulder 175 formed between outer cylindrical wall 173 and the circumferential edge of main body 171.

Main body 171 forms an annular channel 176 between outer cylindrical wall 173 and inner cylindrical wall 174. The outer diameter of channel 176 (adjacent to outer cylindrical wall 173) is sized to accommodate a torque spring 160 when in a resting state (with no load applied), while the inner diameter of channel 176 (adjacent to inner cylindrical wall 174) is no greater than the inner diameter of torque spring 160 when tightened to the greatest extent to be expected during use of the torque driver of the present invention.

A cannula 177 extends centrally through stem 172, main body 171, and inner cylindrical wall 174, and has a diameter corresponding to the outer diameter of sleeve 150.

A hole 178 is formed in main body 174 and extends from the bottom of channel 176 and preferably, though not necessarily, through the entire thickness of main body 171 to an opening at the opposite side thereof. Hole 178 extends parallel to cannula 177 and is radially positioned along the outer circumference of channel 176 adjacent to outer cylindrical wall 173. The diameter of hole 178 is sized to receive end leg 162 of torque spring 160. Optionally, drainage holes 178*a* may also be formed in channel 176 which extend through the thickness of main body 171 to reduce the weight of the torque assembly 200.

A hole 179 is formed on the distal surface of inner cylindrical wall 174 and has a diameter sized to engage a guide pin 190, the purpose of which will be discussed later.

Figure 12:
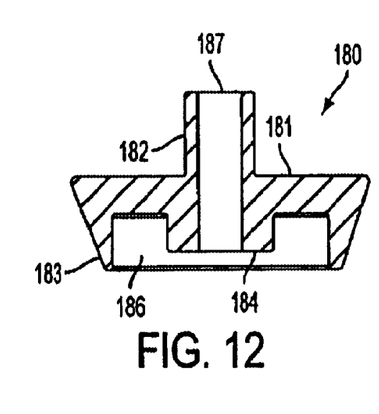
FIG. 12 is a cross-sectional view of the distal cup of the torque assembly in the torque driver.
Figure 13:
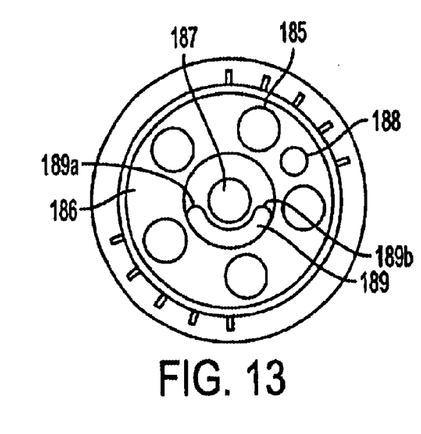
FIG. 13 is a distal elevational view of the distal cup of the torque assembly.

As illustrated in FIGS. 12–13, distal cup 180 of torque assembly 200 is formed as an integral unit having a main body 181, a stem 182 formed on one side of main body 181, outer cylindrical wall 183 formed on the opposite side of main body 181, inner cylindrical wall 184 formed opposite to stem 182 on the same side of main body 181 as outer cylindrical wall 183.

Main body 181 forms an annular channel 186 between outer cylindrical wall 183 and inner cylindrical wall 184. The outer diameter of channel 186 (adjacent to outer cylindrical wall 183) is sized to accommodate insertion of outer cylindrical wall 173 of proximal cup 170, while the inner diameter of channel 186 (adjacent to inner cylindrical wall 174) is no greater than the inner diameter of torque spring 160 when tightened to the greatest extent to be expected during use of the torque driver of the present invention.

A cannula 187 extends centrally through stem 182, main body 181, and inner cylindrical wall 184, and has a diameter corresponding to the outer diameter of the main portion 128 of shaft 120.

A hole 188 is formed in main body 184 in channel 186 and preferably, though not necessarily, extends through the entire thickness of main body 181 to an opening at the opposite side thereof. Hole 188 extends parallel to cannula 187 and has a diameter sized to receive end leg 164 of torque spring 160. Additionally, hole 188 is radially positioned in channel 186 to receive the spring end when the other spring end is inserted into hole 178 of proximal cup 170 and torque spring 160 is at rest (with no load applied). Optionally, drainage holes 185 may also be formed in channel 186 which extend through the thickness of main body 171 to reduce the weight of the torque assembly 200.

An arcuate groove 189 is formed on the proximal surface of inner cylindrical wall 184 and has a width sized to accommodate guide pin 190. The arcuate range of groove 189 corresponds with a maximum range of rotation to be allowed between proximal cup 170 and distal cup 180 of torque assembly 200. The maximum range of rotation, in turn, corresponds with the maximum expected or allowed torque to be applied using the torque driver, taking into consideration the torsional resistance of torque spring 160.

As can be seen in FIG. 7, proximal and distal cups 170 and 180 have cooperating indicia for indicating an amount of torque exerted on torque spring 160 between the cups 170, 180. Distal cup 180 is marked with a scale 220 corresponding to a torque range from 0 to a predetermined maximum quantity. The spacing between scale markings is calibrated according to the spring constant of spring 160, while the arcuate range covered by the scale corresponds that of groove 189. Proximal cup 170 has a singular reference mark 210 for indicating the torque measurement against scale 220.

In each of proximal cup 170 and distal cup 180, the height of the respective outer cylindrical wall 173, 183 is greater than the respective inner cylindrical wall 174, 184 as measured from the base of channel 176,186 so that when the proximal and distal cups are assembled to form the torque assembly 200, the proximal surface of outer cylindrical wall 183 in distal cup 180 abuts against shoulder 175 on proximal cup 170 while the distal surface of inner cylindrical wall 174 abuts against the proximal surface of inner cylindrical wall 184.

In the assembled state of the torque driver 100, shaft 120 is inserted through cannula 187 of distal cup 180 of torque assembly 200 so that a length of the main shaft portion 128 (not including the reduced diameter proximal portion 124) corresponding to the length of the sleeve 150 extends proximally from the distal cup 180. Distal cup 180 is then welded or brazed to the shaft 120 at this position along the length thereof.

Sleeve 150 is inserted into cannula 177 of proximal cup 170 until the distal end thereof is flush with the distal surface of inner cylindrical wall 174, so as to also abut the proximal surface of inner cylindrical wall 184 of distal cup 180. In this position, sleeve 150 is affixed to stem 172 of proximal cup 170 by welding or brazing. Alternatively, sleeve 150 and proximal cup 170 may be formed as an integral piece. The proximal end of shaft 120 is then inserted into the proximal cup 170 and sleeve 150.

Next, the torque assembly 200 is assembled by press fitting the guide pin 190 into hole 179 in proximal cup 170, placing torque spring 160 into annular channel 176 of proximal cup 170 with leg 162 inserted into hole 178, and inserting leg 164 of spring 160 into hole 188 in distal cup 180. Torque assembly 200 is closed by inserting outer cylindrical wall 173 of proximal cup 170 into annular channel 186 inside outer cylindrical wall 183 of distal cup 180, whereupon guide pin 190 should become inserted into end 189a of groove 189 and torque spring 160 becomes encased between annular channels 176 and 186. Also, when torque assembly 200 is closed, the distal surface of inner cylindrical wall 174 of proximal cup 170 abuts the proximal surface of inner cylindrical wall 184 of distal cup 180. Shaft 102 is then prevented by slipping out of sleeve 150 by brazing or welding collar 140 onto the reduced diameter portion 124 at the proximal end of shaft 120.

The assembled unit is then inserted into handle 110, with the proximal surface of collar 140 inserted into stepped bore section 116 and abutting only the radially outermost edge of taper section 115. The minimized contact area between the collar 140 and handle 110 enables the collar 140 and hence shaft 120 to rotate freely within the stepped bore sections 116 and 118.

Sleeve 150 is fixed relative to the handle 110 by a fixing pin inserted into hole 119 in handle 110 and hole 152 in sleeve 150.

Figure 14:
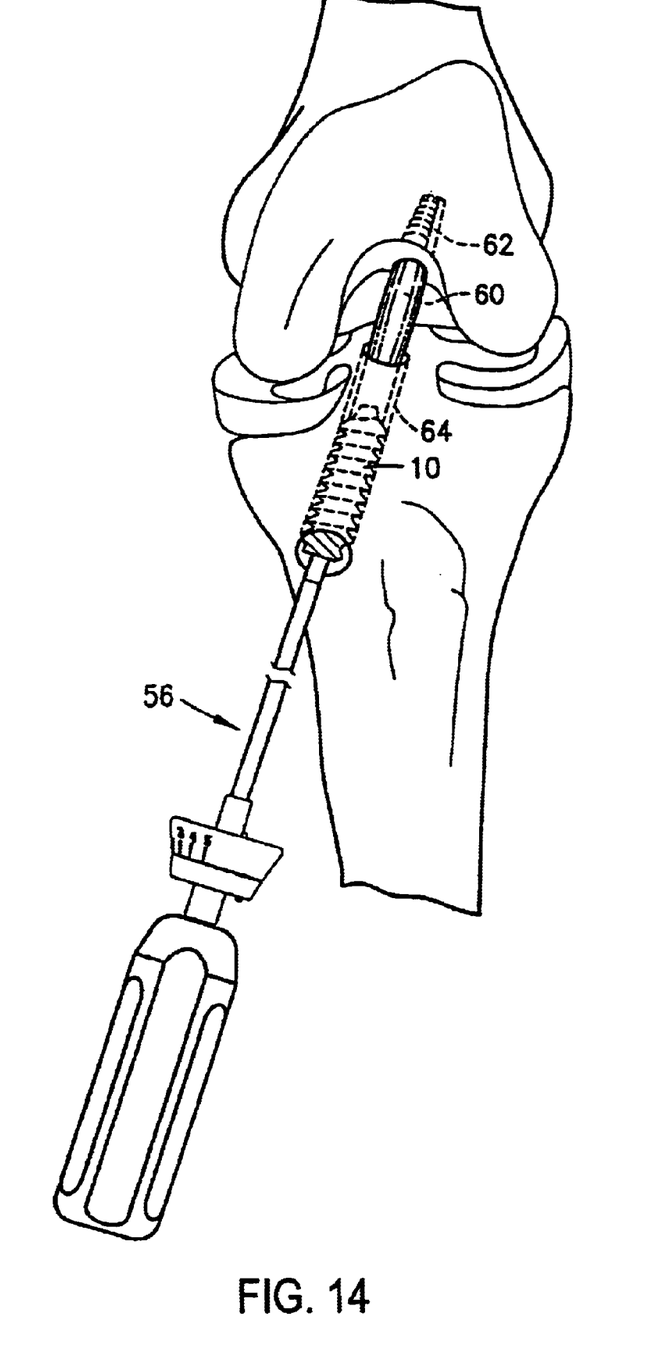
FIG. 14 shows the interference screw of the present invention being inserted into the tibial tunnel against a ligament graft.

Referring now to FIG. 14, the method of endosteal fixation of a ligament graft using an interference screw in accordance with the present invention includes the steps of securing one end of a graft 60 in the femoral socket 62, pulling the opposite end of the graft 60 (extending through the tibial tunnel) taut, and fixating the graft 60 in the tibial tunnel 64 by mounting the bioabsorbable interference screw 10 on torque driver 100 and, using the driver, driving screw 10 in the tibial tunnel against graft 60 to the level of the anterior cortex in the distal portion of the tibial tunnel, such that the interference screw fills all but the top 5–10 mm. of the tunnel, while measuring the torque being applied using the measurement scale 220.

Since the handle 110 is fixedly secured to the sleeve 150 by the fixing pin which in turn is fixedly secured to proximal cup 170, rotation of the handle causes the sleeve 150 and proximal cup to rotate with the same force exerted on the handle 110. At least a portion of the driving force placed on the handle is transferred through the spring 160 and to the distal cup 180 to ultimately drive the interference screw into the bone, since the distal cup 180 is fixedly connected to the shaft 120, which is fixedly connected to the drive head 130. As described above, rotation of the shaft 120 is not inhibited by sleeve 150 or by collar 140 in segment 116 of cannula 111.

The resistance met by the interference screw in entering the tunnel causes the torque spring 160 to tighten. The amount of force from the handle absorbed by the torque assembly to tighten the torque spring depends on the friction resistance between the interference screw and the bone tunnel, and also the spring constant of the coil spring 160. The greater the frictional resistance, the more the coil spring 160 is tightened as the torque exerted on the handle is tightened. In contrast, as the spring constant, i.e., the resistance of the spring against being tightened, increases, a greater portion of the rotational force placed on the handle is translated directly to turning the shaft 160 and drive head 130. Thus, the spring incorporated into the driver of the present invention is selected so as to be able to tightened through a measurable arcuate distance when a torque force in the range yielding a desired fixation strength is achieved.

At rest, with no torque load exerted on the driver, the measurement mark 210 is aligned with the "0" mark on the scale 220, and the guide pin 190 is positioned at end 189*a* of groove 189. When cups 170 and 180 are rotated relative to one another, rotational tension is exerted on the spring, whereupon the measurement of this force is indicated by the mark in scale 220 aligned with measurement mark 210 and corresponds to the amount of torque exerted on spring 160 between cups 170 and 180.

Greater rotational force exerted on handle 110 causes spring 160 to tighten. As spring 160 tightens, the spring exerts increasingly greater resistance to rotation. This resistance is measured as the torque force using the markings 210 and 220.

At the maximum torque load for which the torque driver is designed is reached, the guide pin 190 travels to end 189*b* of groove 189 in distal cup 180, and prevents further relative rotation between the proximal and distal cups. At this point, the measurement marking 210 is prevented from indicating a torque quantity greater than the predetermined amount, thus signaling to the operator that the maximum allowable torque has been reached and enabling the operator to avoid overtorqueing the anchor. If this point is reached, it is possible that a smaller diameter interference screw may be warranted, or that the diameter of the bone tunnel should be increased.

If the highest measurement achieved during installation is less than a predetermined minimum, the fixation strength of the interference screw will be insufficient for proper healing. In this situation, the surgeon should then either replace the interference screw with another having a larger diameter or install a backup fixation device to supplement the fixation strength provided by the interference screw.

After achieving a desired torque measurement or a torque measurement in the desired range using the present invention, driver 66 is then removed, leaving screw 10 in place with an interference fit of up to 1.5 mm, whereupon the surgeon can be confident that the interference screw has been applied with a predetermined amount of torque to optimize the fixation strength of the screw.

In the preferred embodiment, the hole 179 and guide pin 190 are shown radially inward of the spring body 160, but may be positioned radially outward therefrom instead. In further alternatives, other stopping conventions also may be employed without departing from the spirit of the invention.

Figure 15:
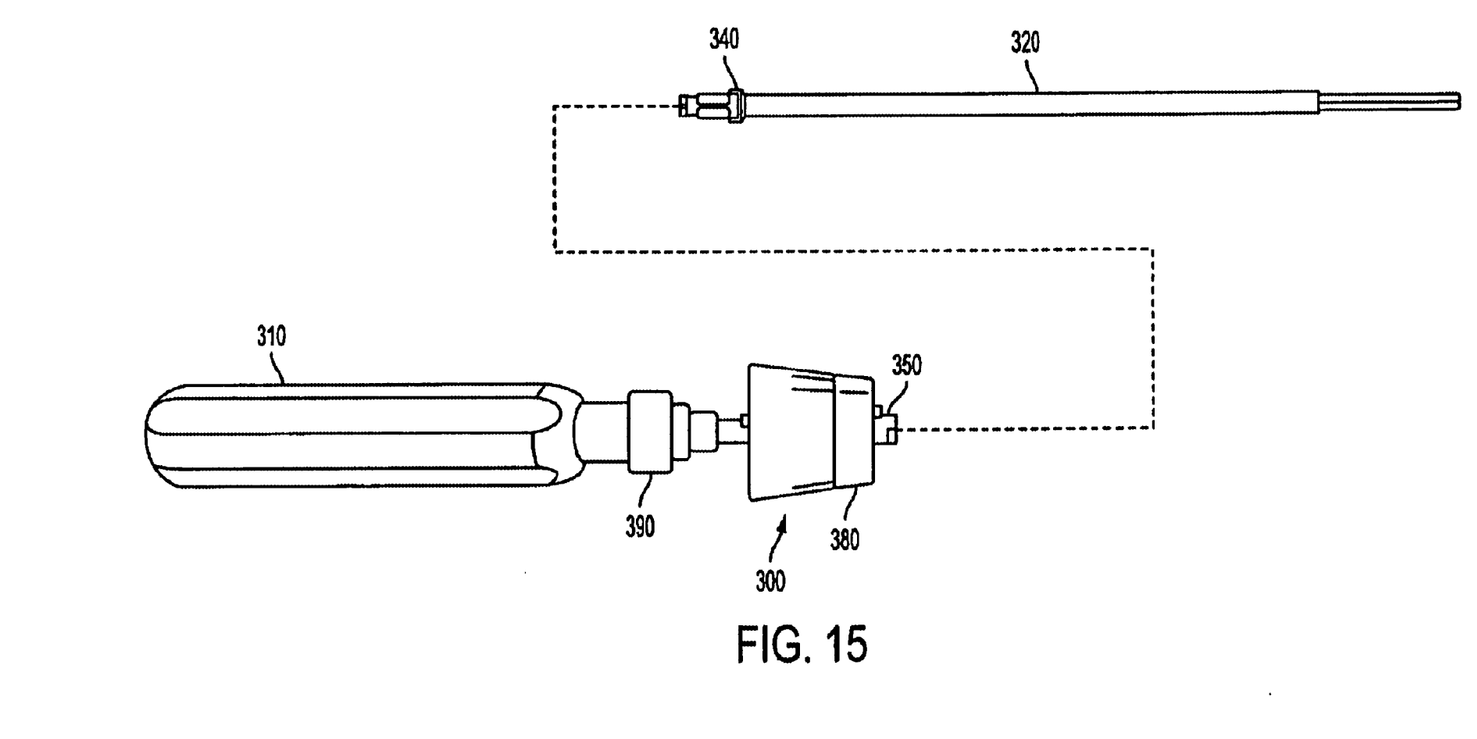
FIG. 15 shows a drive shaft which is releasable from a the torque assembly in a variant of the present invention.

Optionally, the torque driver can be constructed so that the shaft is releasable so as to be interchangeable, to enable use of the driver with different types of tissue anchor or interference screws. An example of a torque assembly usable in this embodiment is shown in FIG. 15. Specifically, the distal side of the distal cup 380 includes a male of female connection socket 350 for releasably engaging a mating connection structure 340 at the proximal end of a drive shaft 320, and the proximal portion of the torque assembly 300 is mountable in the driver handle 310 with a quick-connect fitting 390.

Another optional feature which may be provided in connection with the torque driver of the present invention is a ratchet handle, which only allows an operator to apply torque in one direction. This feature may be implemented according to standard ratcheting mechanisms known to those of ordinary skill in the art, and may be used in combination with the quick-connect feature of the torque assembly and releasable drive shaft construction.

As described above, it is preferred that a tapered, bioabsorbable interference screw is used in connection with the present invention to optimize the fixation strength of the tissue to the bone. Alternatively, the torque driver may be used in the same manner as described herein to install other types of fixation screws such as a conventional, non-tapered interference screw or a headed tissue anchor to secure soft tissue to a bone. With other types of fixation devices, the drive head at the distal end of the torque driver would be appropriately modified or constructed to drivingly engage the selected fixation device.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of securing soft tissue to a bone by interference fixation using an interference screw, said method comprising the steps of:
    forming a tunnel in the bone, said tunnel having a wall;
    inserting the soft tissue in the tunnel;
    positioning the interference screw to be driven into the tunnel;
    using a torque driver to drive the interference screw into the tunnel, wherein the torque driver includes an assembly having a measurement scale for indicating the amount of torque exerted during insertion of the interference screw;
    gauging the amount of torque exerted during the insertion of the interference screw using the measurement scale; and
    determining whether the amount of torque measured by the measurement scale reaches at least a desired minimum value.

2. The method according to claim 1, wherein the interference screw has a diameter relative to the diameter of the bone tunnel formed so as to achieve an interference fit of 1.5 mm upon insertion of the interference screw into the tunnel.

3. The method according to claim 1, wherein if the measured torque is less than the desired minimum value, further comprising exchanging the interference screw with another interference screw having a larger diameter.

4. The method according to claim 1, wherein if the measured torque is less than the desired minimum value, further comprising installing a backup fixation device to supplement the fixation strength of the soft tissue.

5. The method according to claim 1, wherein if the measured torque reaches a maximum value on the measurement scale, further comprising exchanging the interference screw with another interference screw having a smaller diameter.

6. The method according to claim 1, wherein if the measured torque reaches a maximum value on the measurement scale, further comprising widening the diameter of the bone tunnel and re-installing the interference screw.

* * * * *